United States Patent [19]

Josse

[11] 4,075,333
[45] Feb. 21, 1978

[54] STABLE INJECTABLE VITAMIN COMPOSITIONS

[75] Inventor: René Josse, Riedisheim, France

[73] Assignee: Hoffmann-La Roche, Inc., Nutley, N.J.

[21] Appl. No.: 606,383

[22] Filed: Aug. 20, 1975

[30] Foreign Application Priority Data

Feb. 14, 1975 Switzerland .................... 1897/75

[51] Int. Cl.$^2$ ............... A01N 9/28; A61K 31/355; A61K 31/595; A61K 31/07

[52] U.S. Cl. ............................ 424/237; 424/284; 424/344

[58] Field of Search ................ 424/237, 344, 284

[56] References Cited

U.S. PATENT DOCUMENTS

| | | | |
|---|---|---|---|
| 3,070,499 | 12/1962 | Mullins et al. | 424/344 |
| 3,149,037 | 9/1964 | Aiello et al. | 424/344 |
| 3,244,595 | 4/1966 | Feigh | 424/344 |
| 3,639,587 | 2/1972 | Ames | 424/344 |
| 3,708,583 | 1/1973 | Winstrom et al. | 424/344 |
| 3,932,634 | 1/1976 | Kardys | 424/344 |

FOREIGN PATENT DOCUMENTS 1,300,516  12/1972  United Kingdom.

OTHER PUBLICATIONS

Kring et al., Chemical Abstracts 74;6385d, (1971).
Chemical Abstracts 66:105072r, (1967).
Ames, Chemical Abstracts 75:40423v (1971).
Ames, Chemical Abstracts 75:40468p, (1971).
Chemical Abstracts 80: 87465d, (1974).

*Primary Examiner*—Albert T. Meyers
*Assistant Examiner*—D. W. Robinson
*Attorney, Agent, or Firm*—Samuel L. Welt; Bernard S. Leon; William M. Farley

[57] ABSTRACT

Stable, injectable veterinary vitamin compositions containing on a weight basis about 20–55% of vitamin A propionate, 0 to about 1% vitamin D, 0 to about 8% vitamin E, about 10–30% of a non-ionic emulsifier, about 5–45% of a solubilizing agent and about 5–15% isopropanol are disclosed.

9 Claims, No Drawings

STABLE INJECTABLE VITAMIN COMPOSITIONS

BACKGROUND

Numerous injectable compositions are known for use in providing supplemental vitamins to grazing animals such as cattle, sheep, horses and the like. Such preparations are needed paticularly for fat-soluble vitamins because the animals requirements of the vitamins are exceeded by the amount present and available in their daily feed ration.

Known vitamin A propionate containing injectable solutions contain in addition, a non-ionic emulsifier and ethanol. Such solutions are clear and suitable for injection but do not have desirable physical or chemical stability.

Accordingly, there is a need for veterinary vitamin preparations in the form of clear, emulsifiable solutions, which are especially suitable for injection purposes.

DESCRIPTION OF THE INVENTION

According to the present invention, stable, injectable vitamin preparations are provided which contain on a weight basis, about 20-55% of vitamin A proprionate, 0 to about 1% vitamin D component, 0 to about 8% vitamin E component, about 10-30% of a non-ionic emulsifier, about 5-45% of a solubilizing agent and about 5-15% of isopropanol.

Non-ionic emulsifiers which can be used in the present invention are those emulsifiers containing polyoxyethylene groups such as, for example, polyoxyethylated castor oil, commercially available from BASF, Germany under the name Cremophor EL, polyoxyethylenesorbitan monooleate, commercially available under the name Tween 80 from Atlas Chemical, Wilmington, Del., and the like. Polyoxyethylated castor oil is the preferred non-ionic emulsifier. The non-ionic emulsifier can be used in an amount of from about 10 to about 30% by weight, preferably from about 15-25% by weight based on the total volume of the vitamin composition.

Solubilizing agents which can be used in the present invention are of two types. The first type consists of polyol diesters or triglycerides of fatty acids containing 6-14 carbon atoms. A typical representative of this type is commercially available under the name Neobee M20 from Pacific Vegetable Oil Co. San Francisco. The second type consists of monoglycerides of fatty acids containing 6-14 carbon atoms. A representative of this type is commercially available under the name Drewmulse GMC-8 from Drew Chemical, Boonton, N.J. These two types of solubilizing agents can be used not only separately but also in combination. It is preferred to use a combination of the two foregoing types of solubilizing agents, but when only one is used, the monoglycerides of fatty acids containing 6-14 carbon atoms are preferred.

When the solubilizing agent consists solely of polyol diesters or triglycerides of fatty acids containing 6-14 carbon atoms, these are expediently used in an amount of about 5-40% by weight preferably about 15-35% by weight and most preferred about 20-30% by weight based on the total volume of the vitamin composition.

When the solubilizing agent consists solely of monoglycerides of fatty acids containing 6-14 carbon atoms, these are expediently used in an amount of about 5-15% by weight preferably about 8-15% by weight based on the total volume of the vitamin composition.

When a combination of the two groups of solubilizing agents is used, the total amount is expediently about 5 to about 45% by weight preferably about 20-45% by weight, based on the total volume of the vitamin composition. In these combinations, the ratios of the two groups, on a weight basis, are of from about 1,5 to about 3,5 parts, preferably of from about 2 to about 3 parts of polyol diesters or triglycerides of fatty acids for one part of monoglycerides of fatty acids.

The isopropanol is expediently used in an amount of about 5-15% by weight preferably about 5-12% based on the total volume of the vitamin composition.

The vitamin compositions of this invention can contain vitamin A propionate not only alone but also in combination with vitamin D components and/or vitamin E components.

As used herein "vitamin D components", includes all vitamin D active compounds, preferably vitamin $D_2$ (ergocalciferol) and/or vitamin $D_3$ (cholecalciferol). The amount of vitamin D component present when used is expediently about 0.2 to about 1% by weight, preferably about 0.3 to about 0.6%, based on the total volume of the vitamin composition.

As used herein the "vitamin E component", includes all vitamin E active compounds preferably alpha-tocopherol acetate. The amount of vitamin E component present when used is expediently about 3 to about 8% by weight, preferably about 5% by weight based on the total volume of the vitamin composition.

The vitamin compositions provided by the present invention can also contain other ingredients such as, for example, benzyl alcohol and antioxidants. The content of benzyl alcohol when used expediently lies between about 0.5-3% by weight preferably between about 1-2% and especially at about 2%, based on the total volume of the vitamin composition. Examples of antioxidants are, in particular, d,l-alpha-tocopherol, butylated hydroxyanisole, butylated hydroxytoluene, tert.butylhydroquinone (TBHQ) and the like, as well as mixtures thereof. The amount of antioxidant used varies greatly according to the particular antioxidant. Thus, for example, alpha-tocopherol is expediently used in an amount of about 0.5 to about 1.5% by weight and TBHQ in an amount of about 0.02%, these amounts being based on the total volume of the vitamin composition.

At room temperature, the vitamin compositions provided by this invention are clear, anhydrous solutions which can be dispersed in water to form the finest emulsions. The vitamin A content of the compositions of this invention are up to about 1,400,000.

The compositions of this invention can be made by mixing of the various ingredients in a conventional manner. In one convenient procedure, the individual ingredients excluding the isopropanol are first mixed together and the isopropanol is then added. The mixing is expediently carried out under the atmosphere of an inert gas, e.g., nitrogen, argon or the like and at a temperature from about room temperature to about 80° C., preferably at about 65° C. After complete dissolution of ingredients, the mixture is cooled and the isopropanol added.

The following Examples illustrate the invention

EXAMPLE 1

23.2 G. of vitamin A propionate, 5.5 g. of tocopherol acetate, 0.33 g. of vitamin $D_3$, 0.6 g. of d,l-alpha-tocopherol, 16 g. of Cremophor EL, 2 g. of benzyl alcohol, 30 g. of Neobee M20 and 12 g. of Drewmulse GMC-8 are heated to 65° C. under an atmosphere of nitrogen for 5 minutes. The resulting mixture is then cooled to ca 30° C. 5.4 G. of isopropanol are then added under an atmosphere of nitrogen and the resulting mixture is subsequently cooled to room temperature. There is thus obtained a clear solution which contains 654,000 I.U. vitamin A/g.

After storage for 3 months not only at room temperature but also at 45° C., the foregoing solution shows no physical variation whatsoever.

The chemical stability of the foregoing solution is also outstanding since, for example, even with longer storage at an elevated temperature only a slight decrease of the vitamin A activity occurs. This will be evident from the following data:

| | |
|---|---|
| Original vitamin A activity | 654,00 I.U./g. |
| Activity after 3 months at R.T. | 646,000 I.U./g. (99%) |
| Activity after 6 months at R.T. | 635,000 I.U./g. (97%) |
| Activity after 1 month at 45° C. | 611,000 I.U./g. (93%) |
| Activity after 3 months at 45° C. | 524,000 I.U./g. (80%) |
| R.T. = room temperature | |

EXAMPLE 2

23.2 G. of vitamin A propionate, 5.5 g. of tocopherol acetate, 0.33 g. of vitamin $D_3$, 0.6 g. of d,l-alpha-tocopherol, 28 g. of Cremophor EL, 2 g. of benzyl alcohol, 19 g. of Neobee M20 and 10 g. of Drewmulse GMC-8 are heated to 65° C. under a nitrogen atmosphere for 5 minutes. The resulting mixture is then cooled to ca 30° C. 7.8 G. of isopropanol are then added under a nitrogen atmosphere and the resulting mixture is subsequently cooled to room temperature. There is thus obtained a clear solution which contains 632,000 I.U. vitamin A/g.

The foregoing solution has a physical and chemical stability similar to that of the solution manufactured according to Example 1. This is evident from the following data:

| | |
|---|---|
| Original vitamin A activity | 632,000 I.U./g. |
| Activity after 3 months at R.T. | 623,000 I.U./g. (98%) |
| Activity after 6 months at R.T. | 613,000 I.U./g. (97%) |
| Activity after 1 month at 45° C. | 585,000 I.U./g. (92%) |
| Activity after 3 months at 45° C. | 495,000 I.U./g. (78%) |

EXAMPLE 3

46.4 G. of vitamin A propionate, 5.5 g. of tocopherol acetate, 0.66 g. of vitamin $D_3$, 1.2 g. of d,l-alpha-tocopherol, 22 g. of Cremophor EL, 2 g. of benzyl alcohol and 5 g. of Drewmulse GMC-8 are heated to 65° C. under a nitrogen atmosphere for 5 minutes. The resulting mixture is then cooled to ca 30° C. 12.8 G. of isopropanol are then added under a nitrogen atmosphere and the resulting mixture is subsequently cooled to room temperature. There is thus obtained a clear solution which contains 1,245,000 I.U. vitamin A/g.

The foregoing solution has a physical and chemical stability similar to that of the solution manufactured according to Example 1. This is evident from the following data:

| | |
|---|---|
| Original vitamin A activity | 1,245,000 I.U./g. |
| Activity after 3 months at R.T. | 1,225,000 I.U./g. (98%) |
| Activity after 6 months at R.T. | 1,190,000 I.U./g. (95%) |
| Activity after 1 month at 45° C. | 1,130,000 I.U./g. (90%) |
| Activity after 3 months at 45° C. | 915,000 I.U./g. (74%) |

EXAMPLE 4

46.4 G. of vitamin A propionate, 5.5 g. of tocopherol acetate, 0.66 g. of vitamin $D_3$, 1.2 g. of d,l-alpha-tocopherol, 17.5 g. of Cremophor EL, 2 g. of benzyl alcohol and 7 g. of Neobee M20 are heated to 65° C. under a nitrogen atmosphere for 5 minutes. The resulting mixture is then cooled to ca 30° C. 13.6 G. of isopropanol are then added under a nitrogen atmosphere and the resulting mixture is subsequently cooled to room temperature. There is thus obtained a clear solution which contains 1,340,000 I.U. vitamin A/g.

The foregoing solution has a physical and chemical stability similar to that of the solution manufactured according to Example 1. This is evident from the following data:

| | |
|---|---|
| Original vitamin A activity | 1,340,000 I.U./g. |
| Activity after 3 months at R.T. | 1,300,000 I.U./g. (97%) |
| Activity after 6 months at R.T. | 1,230,000 I.U./g. (92%) |
| Activity after 1 month at 45° C. | 1,205,000 I.U./g. (90%) |
| Activity after 3 months at 45° C. | 1,080,000 I.U./g. (80%) |

I claim:

1. A stable injectable vitamin composition comprising on a weight to volume basis about 20–55% of vitamin A propionate, 0 to about 1% vitamin D component, 0 to about 8% vitamin E component, about 10–30% of a non-ionic emulsifier containing polyoxyethylene groups, about 5–45% of a solubilizing agent selected from the group consisting of polyoldiesters, triglycerides or monoglycerides of fatty acids containing 6–14 carbon atoms and mixtures thereof, and about 5–15% of isopropanol.

2. The vitamin composition of claim 1, wherein the non-ionic emulsifier is polyoxyethylated castor oil.

3. The vitamin composition of claim 1, wherein the non-ionic emulsifier is present in an amount of about 5–25%.

4. The vitamin composition of claim 1, which contains about 5–40% on a weight to volume basis of polyol diesters or triglycerides of fatty acids containing 6–14 carbon atoms.

5. The vitamin composition of claim 1, which contains about 15–35% on a weight to volume basis of polyol diesters or triglycerides of fatty acids containing 6–14 carbon atoms.

6. The vitamin composition of claim 1, which contains on a weight to volume basis about 20–30% of polyol diesters or triglycerides of fatty acids containing 6–14 carbon atoms.

7. The vitamin composition of claim 1, which contains on a weight to volume basis about 5–15% of monoglycerides of fatty acids containing 6–14 carbon atoms.

8. The vitamin composition of claim 7, which contains on a weight to volume basis about 8–15% of monoglycerides of fatty acids containing 6–14 carbon atoms.

9. The vitamin composition of claim 1 containing on a weight to volume basis about 5–12% of isopropanol.

* * * * *